United States Patent
Regensburger et al.

(10) Patent No.: US 11,468,569 B2
(45) Date of Patent: Oct. 11, 2022

(54) PROVIDING A PROGNOSIS DATA RECORD

(71) Applicant: Siemens Healthcare GmbH, Erlangen (DE)

(72) Inventors: Alois Regensburger, Erlangen (DE); Michael Wiets, Langensendelbach (DE); Sabrina Walter, Bamberg (DE); Amilcar Alzaga, Bayern (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/016,303

(22) Filed: Sep. 9, 2020

(65) Prior Publication Data

US 2021/0073993 A1    Mar. 11, 2021

(30) Foreign Application Priority Data

Sep. 11, 2019   (DE) ...................... 10 2019 213 813.6

(51) Int. Cl.
| | |
|---|---|
| *G06T 7/00* | (2017.01) |
| *A61B 8/08* | (2006.01) |
| *G06V 10/25* | (2022.01) |

(52) U.S. Cl.
CPC ............ *G06T 7/0016* (2013.01); *A61B 8/485* (2013.01); *G06V 10/25* (2022.01); *G06T 2207/20081* (2013.01)

(58) Field of Classification Search
CPC ......... G06T 7/0016; G06T 2207/20081; A61B 8/485; G06K 9/3233

(Continued)

(56) References Cited

U.S. PATENT DOCUMENTS

| | | | |
|---|---|---|---|
| 2004/0101181 A1* | 5/2004 | Giger ...................... | G06T 7/187 382/128 |
| 2013/0296743 A1* | 11/2013 | Lee ......................... | G16H 50/30 601/3 |
| 2018/0168552 A1 | 6/2018 | Shi | |

FOREIGN PATENT DOCUMENTS

| | | |
|---|---|---|
| DE | 102013007136 A1 | 11/2013 |
| WO | 2019232009 A1 | 12/2019 |

OTHER PUBLICATIONS

German Office Action for German Application No. 10 2019 213 813.6 dated Aug. 11, 2020.

(Continued)

*Primary Examiner* — Wednel Cadeau
(74) *Attorney, Agent, or Firm* — Lempia Summerfield Katz LLC

(57) ABSTRACT

A method for providing a prognosis data record includes receiving a first image data record relating to an examination region of an examination object, and receiving an operating parameter of a medical object that is arranged at the examination region of the examination object and positioning information of the medical object that is arranged at the examination region. The prognosis data record is created by applying a trained function to input data. The input data is based on the first image data record, the at least one operating parameter, and the positioning information of the medical object. At least one parameter of the trained function is based on a comparison with a first comparison image data record. As compared with the first image data record, the first comparison image data record includes changes influenced by the medical object at the examination region. The prognosis data record is provided.

17 Claims, 6 Drawing Sheets

(58) Field of Classification Search
USPC .......................................................... 382/128
See application file for complete search history.

(56) References Cited

OTHER PUBLICATIONS

Maier, Andreas, et al. "A gentle introduction to deep learning in medical image processing." Zeitschrift für Medizinische Physik 29.2 (2019): 86-101.
Regensburger, Alois "Imaging for blood flow measurement for ablation planning" Prior Art Journal, pp. 79-81, 2019 ISBN: 978-3-947591-04-6 , with English translation.

* cited by examiner

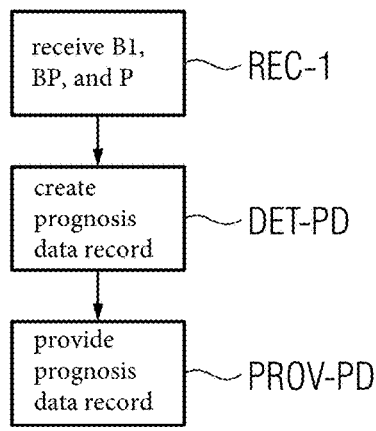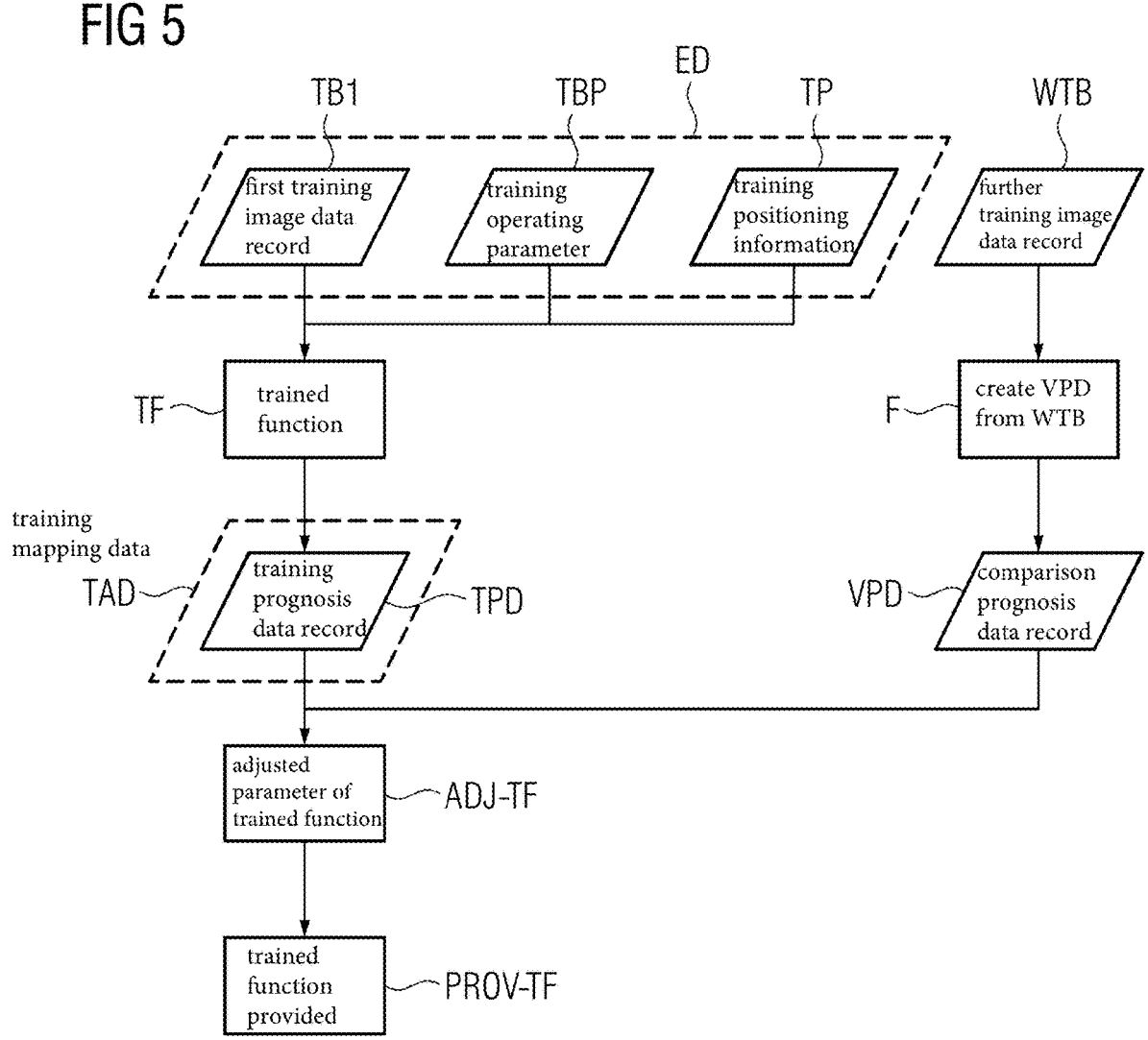

PROVIDING A PROGNOSIS DATA RECORD

This application claims the benefit of German Patent Application No. DE 10 2019 213 813.6, filed on Sep. 11, 2019, which is hereby incorporated by reference in its entirety.

BACKGROUND

The present embodiments relate to providing a prognosis data record relating to an examination object.

In the field of medical practice, particularly precise and, for example, comprehensive support for a medical professional (e.g., a doctor) is critical to good treatment success. In this case, the medical professional may be supported in the context of both treatment and diagnosis using, for example, medical imaging for a section requiring treatment in an examination object (e.g., in a human and/or animal patient).

For example, in the case of medical interventions in which tissue is to be ablated by a medical object (e.g., an ablation needle and/or a laparoscope and/or endoscope), accurate knowledge of the ablation surface or the ablation zone is critical. In this case, the characteristic form of the ablation zone may often be heavily dependent on a property of the respective tissue and on the medical object.

The prior art discloses methods for simulating an ablation zone based on preoperatively recorded three-dimensional imaging data for the examination object and intraoperative blood flow imaging. In this case, assumptions relating to tissue parameters are often also made based on the preoperatively recorded image data. The assumptions may have a disadvantageous effect on the accuracy of the simulated ablation zone.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a particularly accurate prognosis for an examination region that may be influenced by a medical object is provided.

A computer-implemented method for providing a prognosis data record relating to an examination object, a computer-implemented method for providing a trained function, a training unit, a provision unit, a medical device, a computer program product, and a computer-readable storage medium are provided. Advantageous embodiment variants with appropriate developments are also specified.

Apparatuses and methods are provided. Features, advantages, or alternative embodiment variants of one subject matter may also be applied equally to the other subject matter and vice versa.

Both methods and apparatuses for providing a prognosis data record, and methods and apparatuses for providing trained functions are provided. In this context, features and alternative embodiment variants of data structures and/or functions relating to methods and apparatuses for providing a prognosis data record may be transferred to similar data structures and/or functions relating to methods and apparatuses for providing trained functions. Similar data structures may be identified in this context, for example, by using the prefix "training". Further, the trained functions that are used in methods and apparatuses for providing a prognosis data record relating to an examination object may be adjusted and/or provided, for example, by methods and apparatuses for providing trained functions.

In a first aspect, a computer-implemented method for providing a prognosis data record relating to an examination object is provided. According to this, provision is made for receiving a first image data record relating to an examination region of the examination object. In addition to this, at least one operating parameter of a medical object that is arranged at the examination region of the examination object, and positioning information of the medical object that is arranged at the examination region of the examination object are received. In addition, the prognosis data record is created by applying a trained function to input data. In this case, the input data is based on the first image data record and on the at least one operating parameter and the positioning information of the medical object. In addition to this, at least one parameter of the trained function is based on a comparison with a first comparison image data record. In this case, as compared with the first image data record, the first comparison image data record includes changes influenced by the medical object at the examination region. After this, the prognosis data record is provided.

The first image data record may include, for example, two-dimensional and/or three-dimensional medical image data relating to the examination region of the examination object. The first image data record may map the examination region of the examination object (e.g., preoperatively). In this case, the first image data record may include a tissue parameter map, for example. In addition to this, a predetermined tissue region (e.g., a tumor) may be segmented in the first image data record.

In addition to this, the examination region of the examination object may include an anatomical and/or spatial region of the examination object. The examination region may be influenced by the medical object and/or includes a predetermined tissue region (e.g., a tumor).

In this case, the first image data record relating to the examination region of the examination object may be recorded and/or provided by a medical imaging device, for example. The examination object may be, for example, an animal patient and/or a human patient in this case.

The medical imaging device may take the form of, for example, a medical x-ray device (e.g., a C-arm x-ray device and/or DynaCT) and/or a magnetic resonance system (MRT) and/or a computed tomography system (CT) and/or an ultrasound device.

Further, the first image data record may include metadata. In this case, the metadata may include information about recording parameters and/or operating parameters of the medical imaging device and/or patient data.

The receipt of the first image data record may include, for example, capture and/or readout from a computer-readable data store and/or receipt from a data storage unit (e.g., a database). In addition to this, the first image data record may be provided by a processing unit of the medical imaging device.

The medical object may include, for example, an ablation needle and/or a laparoscope and/or an endoscope and/or an electro-cauterizer and/or a catheter.

The receipt of the at least one operating parameter of the medical object that is arranged at the examination region of the examination object may include, for example, capture and/or readout from a computer-readable data store and/or receipt from a data storage unit (e.g., a database). In addition to this, the at least one operating parameter may be provided by a processing unit of the medical object.

In this case, the at least one operating parameter may include an electrical current strength and/or electrical voltage and/or a temperature and/or a magnetic field strength and/or an electrical field strength and/or frequency of the medical object.

In addition to this, the positioning information of the medical object that is arranged at the examination region of the examination object may include information about the orientation and/or alignment and/or position of the medical object (e.g., relative to the examination region of the examination object and/or to the medical imaging device for recording the first image data record). In addition to this, it is possible to determine an orientation and/or alignment and/or position of the medical object relative to the first image data record based on the positioning information (e.g., by registration).

In addition to this, the positioning information may be determined by a medical imaging device (e.g., a medical x-ray device and/or a magnetic resonance system and/or a computed tomography system and/or an ultrasound device and/or a camera system and/or an electromagnetic location-finding system). In this case, the positioning information may be calculated, for example, by segmenting the medical object in a mapping of the medical object by the medical imaging device. In addition to this, the positioning information may be determined by the medical imaging device using, for example, a marker structure and/or arranging at least one marker object at the medical object.

The receipt of the positioning information of the medical object that is arranged at the examination region of the examination object may include, for example, capture and/or readout from a computer-readable data store and/or receipt from a data storage unit (e.g., a database). In addition to this, the positioning information may be provided by a processing unit of the medical object. For this, the medical object may have, for example, a position sensor (e.g., a gyroscope).

Further, the trained function may be trained by a machine learning method. For example, the trained function may be a neural network (e.g., a convolutional neural network (CNN) or a network including a convolutional layer).

A trained function maps input data onto output data. In this context, the output data may also depend, for example, on one or more parameters of the trained function. The one or more parameters of the trained function may be determined and/or adjusted by training. The determination and/or adjustment of the one or more parameters of the trained function may be based, for example, on a pair of training input data and associated training output data, where the trained function for creating training mapping data is applied to the training input data. For example, the determination and/or adjustment may be based on a comparison of the training mapping data with the training output data. A trainable function (e.g., a function with one or more parameters that have not yet been adjusted) is generally also referred to as a trained function.

Other terms for trained function include trained mapping rule, mapping rule with trained parameters, function with trained parameters, algorithm based on artificial intelligence, and machine-learning algorithm. An example of a trained function is an artificial neural network, where arc weights of the artificial neural network correspond to the parameters of the trained function. For example, a trained function may also be a deep artificial neural network (e.g., a deep neural network). A further example of a trained function is a "support vector machine", and, for example, other machine learning algorithms may also be used as a trained function.

The trained function (e.g., the neural network) has an input layer and an output layer. In this case, the input layer may be configured to receive input data. In addition to this, the output layer may be configured to provide mapping data. In this case, the input layer and/or the output layer may each include a plurality of channels (e.g., neurons).

The prognosis data record is determined by applying the trained function to the input data. In this case, the input data is based on the first image data record and on the at least one operating parameter and the positioning information of the medical object. In addition to this, at least one parameter of the trained function may be based on a comparison with a first comparison image data record. In this case, as compared with the first image data record, the first comparison image data record includes changes influenced by the medical object at the examination region.

The first comparison image data record may include, for example, two-dimensional and/or three-dimensional medical image data relating to the examination region of the examination object. The first comparison image data record may map the examination region of the examination object (e.g., postoperatively). In this case, the first comparison image data record may include a tissue parameter map, for example. In addition to this, a predetermined tissue region (e.g., an ablation zone and/or ablation lesion) may be segmented and/or contrasted in the first comparison image data record. In this case, the predetermined tissue region may include, for example, changes influenced by the medical object.

For example, the at least one parameter of the trained function may be based on a comparison of a further prognosis data record (e.g., a training prognosis data record) with the first comparison image data record. The further prognosis data record in this case may have been determined, for example, by applying the trained function to input data. The input data is based on a further first image data record and on at least one further operating parameter and further positioning information of the medical object. In this case, the training prognosis data record may be determined, for example, as part of a proposed computer-implemented method for providing a trained function, which is described below.

In addition to this, the prognosis data record may correspond, for example, to a comparison image data record, where a predetermined tissue region of the examination region (e.g., an ablation zone and/or ablation lesion) may be segmented and/or contrasted in the prognosis data record. In addition to this, the prognosis data record may include information about a change influenced by the medical object at the examination region (e.g., the predetermined tissue region).

The provision of the prognosis data record may include, for example, storage on a computer-readable storage medium and/or output to a presentation unit and/or transfer to a processing unit.

By this, a medical professional may be supported by the provision of a particularly precise and comprehensive prognosis in relation to a change influenced by the medical object at the examination region of the examination object.

In a further embodiment variant of the proposed computer-implemented method for providing a prognosis data record, an elastography data record relating to the examination region of the examination object may be received. In addition to this, the elastography data record may be registered with the first image data record. In addition, the input data may also be based on the elastography data record.

In this case, the elastography data record may include information about an elasticity and/or viscosity of at least one tissue region of the examination region. For example, the elastography data record may include an assignment of an elastography value and/or elastography information to at least one tissue region. This is contained in the examination region, for example. The elastography data record may include, for example, two-dimensional and/or three-dimensional medical image data relating to the examination region of the examination object. The elastography data record may map the examination region of the examination object (e.g., preoperatively).

In this case, the elastography data record relating to the examination region of the examination object may be recorded and/or provided, for example, by a medical imaging device (e.g., preoperatively). The medical imaging device for recording the elastography data record may take the form of a magnetic resonance system (MRT) and/or an ultrasound device, for example.

The receipt of the elastography data record may include, for example, capture and/or readout from a computer-readable data store and/or receipt from a data storage unit (e.g., a database). In addition to this, the elastography data record may be provided by a processing unit of the medical imaging device for recording the elastography data record.

The input data of the trained function may also be based on the elastography data record. As a result of taking the elastography data record into account when creating the prognosis data record, greater accuracy of the prognosis data record may be achieved with respect to a change influenced by the medical object at the examination region.

In addition to this, the registration of the elastography data record with the first image data record may be based, for example, on a specified anatomical structure and/or a predetermined tissue region (e.g., an ablation zone and/or ablation lesion) and/or a marker structure. In this case, the registration of the elastography data record with the first image data record may include a rigid and/or non-rigid transformation of the elastography data record. For example, the registration of the elastography data record with the first image data record may be effected in an image-based manner (e.g., based on anatomical and/or geometrical features).

In a further embodiment variant of the proposed computer-implemented method for providing a prognosis data record, at least one second image data record relating to at least one section of the examination region of the examination object may be received. In this case, the at least one second image data record may map a temporal change at the examination region of the examination object as a result of the medical object. In addition to this, the input data may also be based on the at least one second image data record.

The at least one second image data record may include, for example, two-dimensional and/or three-dimensional medical image data relating to at least one section of the examination region of the examination object. The at least one second image data record may map the at least one section of the examination region of the examination object (e.g., intraoperatively). In addition, the at least one second image data record may include, for example, a tissue parameter map and/or a temperature map. In this case, the at least one second image data record may map a temporal change at the examination region of the examination object as a result of the medical object (e.g., as compared with the first image data record). In addition to this, a predetermined and/or changed tissue region (e.g., an ablation zone and/or an ablation lesion) may be segmented and/or contrasted in the at least one second image data record.

In this case, the at least one second image data record relating to the examination region of the examination object may be recorded and/or provided, for example, by a medical imaging device. The medical imaging device for recording the at least one second image data record may take the form of, for example, a medical x-ray device (e.g., a C-arm x-ray device and/or DynaCT, and/or magnetic resonance system (MRT) and/or computed tomography system (CT) and/or ultrasound device).

The receipt of the at least one second image data record may include, for example, capture and/or readout from a computer-readable data store and/or receipt from a data storage unit (e.g., a database). In addition to this, the at least one second image data record may be provided by a processing unit of the medical imaging device for recording the at least one second image data record.

In addition to this, the at least one second image data record may be registered with the first image data record. In this case, the registration of the at least one second image data record with the first image data record may be based, for example, on a specified anatomical structure and/or a predetermined tissue region (e.g., an ablation zone and/or ablation lesion, and/or a marker structure). In this case, the registration of the at least one second image data record with the first image data record may include a rigid and/or non-rigid transformation of the at least one second image data record. For example, the registration of the at least one second image data record with the first image data record may be effected in an image-based manner (e.g., based on anatomical and/or geometrical features).

The input data of the trained function may also be based on the at least one second image data record. As a result of taking the second image data record into account when creating the prognosis data record, greater accuracy of the prognosis data record may be achieved with respect to a temporal change influenced by the medical object at the examination region.

In a further embodiment variant of the proposed computer-implemented method for providing a prognosis data record, the at least one second image data record may be recorded by an ultrasound device. In this case, the at least one second image data record may include, for example, two-dimensional and/or three-dimensional medical ultrasound image data relating to at least one section of the examination region of the examination object. In addition to this, a predetermined change of a tissue region that may be influenced by the medical object (e.g., an ablation zone and/or an ablation lesion and/or at least one fluid blister or bubble) may be segmented and/or contrasted in the at least one second image data record. A fluid bubble may occur, for example, in the case of a thermal ablation of a tissue region by the medical object as a result of local heat action. In this case, the at least one fluid bubble may include, for example, a spatially enclosed fluid (e.g., a gas and/or gas mixture and/or a liquid and/or a liquid mixture).

By this, a lesion formation (e.g., an ablation lesion) and/or a fluid bubble formation (e.g., as a temporal change at the examination region of the examination object) may be mapped in the at least one second image data record.

In this case, positioning information of the ultrasound device at the instant of the recording of the second image data record may be captured by a position capturing unit (e.g., an electromagnetic and/or optical sensor). By this, it is possible to achieve a particularly accurate registration of the at least one second image data record with the first image data record.

In a further embodiment variant of the proposed computer-implemented method for providing a prognosis data record, a plurality of second image data records may be received in temporal sequence. In this case, a prognosis data record may be created in each case based on the second image data records previously received in the temporal sequence.

In this case, the plurality of second image data records may be recorded by one or various medical imaging devices. By this, it is possible to achieve a particularly comprehensive mapping of the temporal change at the examination region of the examination object as a result of the medical object.

In addition to this, the act of creating the prognosis data record by applying the trained function to input data may be repeated (e.g., iteratively) following the receipt of a second image data record in each case. In this case, the input data of the trained function may be created in each case based on the second image data records previously received in the temporal sequence. For example, the input data for creating a prognosis data record may be based on all second image data records previously received in the temporal sequence. By this, a continuous improvement of the accuracy of the prognosis data records may be achieved. For example, a temporal profile of the change at the examination region of the examination object as a result of the medical object, previously captured in the temporal sequence by the plurality of second image data records, may be taken into account when creating the respective prognosis data record.

The receipt of the plurality of second image data records may include, for example, capture and/or readout from a computer-readable data store and/or receipt from a data storage unit (e.g., a database). In addition to this, the plurality of second image data records may be provided by a processing unit of the medical imaging device for recording the plurality of second image data records. For example, all second image data records previously recorded in the temporal sequence may be stored in the processing unit and/or a data storage unit and/or a computer-readable data store.

In a further embodiment variant of the proposed computer-implemented method for providing a prognosis data record, the prognosis data record may include probability information and/or characteristic form information (e.g., about the temporal profile) of a fluid bubble formation and/or lesion formation within the examination region of the examination object. In this case, the probability information may include, for example, a temporal and/or spatial progression model of the fluid bubble formation and/or lesion formation within the examination region of the examination object. For example, the prognosis data record may include an assignment of in each case at least one probability value of a fluid bubble formation and/or lesion formation to at least one tissue region within the examination region. In addition to this, the prognosis data record may include characteristic form information (e.g., a volume model) about a characteristic form of the fluid bubble formation and/or lesion formation within the examination region.

In this case, a fluid bubble may include, for example, a spatially enclosed fluid (e.g., a gas and/or gas mixture and/or a liquid and/or a liquid mixture). In addition to this, a lesion and/or fluid bubble may be captured and/or presented, for example, by changed contrasting in at least one tissue region of the examination region as compared with the first image data record.

In this case, a probability of fluid bubble formation and/or lesion formation within the examination region may be dependent on, for example, a thermal capacity and/or thermal conductivity and/or elasticity and/or viscosity of the tissue region. In addition to this, the probability of fluid bubble formation and/or lesion formation within the examination region may be dependent on the at least one operating parameter of the medical object.

In this case, for example, all input data of the trained function may be taken into account for the purpose of improving an accuracy of the prognosis data record. In this case, interpolation of the probability information and/or characteristic form information (e.g., in tissue regions of the examination region in which little or no fluid bubble formation and/or lesion formation is possible) may also be advantageous. For this, the prognosis data record may be interpolated by applying, for example, an interpolation function. In addition to this, the prognosis data record may be extrapolated by applying an extrapolation function (e.g., including a simulation of the probability information and/or characteristic form information) in, for example, tissue regions of the examination region. In this case, a temperature profile, for example, may be extrapolated around the medical object. In addition to this, the extrapolation may be based on, for example, an exponential and/or Gaussian temperature gradient around the medical object. Based on at least one tissue parameter of the examination region (e.g., a thermal conductivity coefficient), the temperature profile around the medical object may be determined (e.g., by convolution of a spatial heat effect originating from the medical object with the temperature gradient of the tissue region of the examination object).

In a further embodiment variant of the proposed computer-implemented method for providing a prognosis data record, the prognosis data record may have a validity range with respect to the at least one operating parameter. The trained function for creating the prognosis data record has been trained according to a proposed computer-implemented method for providing a trained function. In this case, using, for example, the at least one training operating parameter as input data (e.g., training input data), a validity range (e.g., a definition range of the trained function) may be specified for the prognosis data records that may be created. For example, an electrical current-strength range and/or an electrical voltage range and/or a temperature range and/or a magnetic field-strength range and/or an electrical field-strength range and/or a frequency range of the at least one training operating parameter of the respective medical object may specify the validity range of the prognosis data record.

In addition to this, the prognosis data record may include information about the validity range with respect to the at least one operating parameter. In this case, irrespective of the validity range, for example, a prognosis data record may be created by applying the trained function to input data. With reference to the information about the validity range contained in the prognosis data record, it is possible to infer the validity of the prognosis data record with respect to the at least one operating parameter. For example, the information about the validity range of the prognosis data record may be output to an operator by a presentation unit.

In a further embodiment variant of the proposed computer-implemented method for providing a prognosis data record, the first image data record may be recorded by a magnetic resonance system and/or a medical x-ray device and/or a computed tomography system. By this, a two-dimensional and/or three-dimensional mapping of the examination region of the examination object may be achieved in the first image data record (e.g., preoperatively).

In a second aspect, the present embodiments relate to a computer-implemented method for providing a trained function. In this case, a first training image data record relating to an examination region of an examination object is received. In addition to this, at least one training operating parameter of a medical object that is arranged at the examination region of the examination object and training positioning information of the medical object that is arranged at the examination region of the examination object are received. Further, a further training image data record relating to the examination region of the examination object is received. In this case, the further training image data record is recorded after the first training image data record in time, where a change at the examination region of the examination object as a result of the medical object takes place after the recording of the first training image data record and before recording the further training image data record. In addition, a further comparison prognosis data record is created from the further training image data record. In this case, as compared with the first training image data record, the further comparison prognosis data record includes changes influenced by the medical object at the examination region. In addition to this, a training prognosis data record is created by applying the trained function to input data. In this case, the input data is based on the first training image data record and on the at least one training operating parameter and the training positioning information of the medical object. After this, at least one parameter of the trained function is adjusted based on a comparison of the further comparison prognosis data record and the training prognosis data record. In addition to this, the trained function is provided.

The first training image data record may have, for example, all the properties of the first image data record as described above in relation to the method for providing a prognosis data record and vice versa. For example, the first training image data record may be a first image data record. The first training image data record may include, for example, two-dimensional and/or three-dimensional medical image data relating to the examination region of the examination object. The first training image data record may map the examination region of the examination object (e.g., preoperatively). In this case, the first training image data record may include, for example, a tissue parameter map. In addition to this, a predetermined tissue region (e.g., a tumor) may be segmented in the first training image data record.

In addition to this, the examination region of the examination object may include an anatomical and/or spatial region of the examination object. The examination region may be influenced by the medical object and/or includes a predetermined tissue region (e.g., a tumor).

In this case, the first training image data record relating to the examination region of the examination object may be recorded and/or provided by a medical imaging device, for example. The examination object may be, for example, an animal patient and/or a human patient in this case.

The medical imaging device may take the form of, for example, a medical x-ray device (e.g., a C-arm x-ray device and/or DynaCT) and/or a magnetic resonance system (MRT) and/or a computed tomography system (CT) and/or an ultrasound device.

Further, the first training image data record may include metadata. In this case, the metadata may include information about recording parameters and/or operating parameters of the medical imaging device for recording the first training image data record.

The receipt of the first training image data record may include, for example, capture and/or readout from a computer-readable data store and/or receipt from a data storage unit (e.g., a database). In addition to this, the first training image data record may be provided by a processing unit of the medical imaging device for recording the first training image data record.

The medical object may include, for example, an ablation needle and/or a laparoscope and/or an endoscope and/or an electro-cauterizer and/or a catheter.

The at least one training operating parameter may have, for example, all the properties of the at least one operating parameter as described above in relation to the method for providing a prognosis data record and vice versa. For example, the at least one training operating parameter may be an operating parameter. The receipt of the at least one training operating parameter of the medical object that is arranged at the examination region of the examination object may include, for example, capture and/or readout from a computer-readable data store and/or receipt from a data storage unit (e.g., a database). In addition to this, the at least one training operating parameter may be provided by a processing unit of the medical object.

In this case, the at least one operating parameter may include an electrical current strength and/or electrical voltage and/or a temperature and/or a magnetic field strength and/or an electrical field strength and/or frequency of the medical object.

The training positioning information may have, for example, all the properties of the positioning information as described above in relation to the method for providing a prognosis data record and vice versa. For example, the training positioning information may be positioning information. In addition to this, the training positioning information of the medical object that is arranged at the examination region of the examination object may include information about the orientation and/or alignment and/or position of the medical object (e.g., relative to the examination region of the examination object and/or to the medical imaging device for recording the first training image data record). In addition to this, it is possible to determine an orientation and/or alignment and/or position of the medical object relative to the first training image data record based on the training positioning information (e.g., using registration).

In addition to this, the training positioning information may be determined by a medical imaging device (e.g., a medical x-ray device and/or a magnetic resonance system and/or a computed tomography system and/or an ultrasound device and/or a camera system and/or an electromagnetic location-finding system). In this case, the training positioning information may be calculated, for example, by segmenting the medical object in a mapping of the medical object by the medical imaging device. In addition to this, the training positioning information may be determined by the medical imaging device using, for example, a marker structure and/or arranging at least one marker object at the medical object.

The receipt of the training positioning information of the medical object that is arranged at the examination region of the examination object may include, for example, capture and/or readout from a computer-readable data store and/or receipt from a data storage unit (e.g., a database). In addition to this, the training positioning information may be provided by a processing unit of the medical object. For this, the medical object may have, for example, a position sensor (e.g., a gyroscope).

The further training image data record may include, for example, two-dimensional and/or three-dimensional medical image data relating to at least one section of the examination region of the examination object. The further training image data record may map the at least one section of the examination region of the examination object (e.g., postoperatively). In this case, the further training image data record may include, for example, a tissue parameter map. In this case, the further training image data record may be recorded after the first training image data record in time. In addition, a change at the examination region of the examination object as a result of the medical object may take place after the recording of the first training image data record and before recording the further training image data record.

The receipt of the further training image data record may include, for example, capture and/or readout from a computer-readable data store and/or receipt from a data storage unit (e.g., a database). In addition to this, the further training image data record may be provided by a processing unit of the medical imaging device for recording the further training image data record.

The creation of the comparison prognosis data record from the further training image data record may include, for example, a registration of the further training image data record with the first training image data record. In this case, the registration of the further training image data record with the first training image data record may be based, for example, on a specified anatomical structure and/or a predetermined tissue region (e.g., an ablation zone and/or ablation lesion) and/or a marker structure. In this case, the registration of the further training image data record with the first training image data record may include a rigid and/or non-rigid transformation of the further training image data record. For example, the registration of the further training image data record with the first image data record may be effected in an image-based manner (e.g., based on anatomical and/or geometrical features).

Further, the creation of the comparison prognosis data record may include a segmentation and/or contrasting of the change at the examination region of the examination object as a result of the medical object in the further training image data record. In addition to this, the creation of the comparison prognosis data record may include a correlation and/or a subtraction of the further training image data record and the first training image data record.

By this, it is possible for the change at the examination region of the examination object as a result of the medical object to be captured.

The training prognosis data record may be determined by applying the trained function to the input data. In this case, the input data may be based on the first training image data record and on the at least one training operating parameter and the training positioning information of the medical object. In addition to this, at least one parameter of the trained function may be based on a comparison of the comparison prognosis data record with the training prognosis data record.

In addition to this, the first training image data record and/or the further training image data record and/or the at least one training operating parameter and/or the training positioning information may be simulated. For example, the at least one training operating parameter may be simulated for various medical objects. In addition to this, the first and/or the further medical training data record may be simulated for various tissue types and/or tissue regions within the examination region of the examination object. Further, the further training image data record may be simulated for various changes at the examination region of the examination object as a result of the medical object. In addition, the training positioning information may be simulated for various medical objects and/or arrangements of medical objects and/or various examination objects.

Further, the provision of the trained function may include, for example, storage on a computer-readable storage medium and/or transfer to a processing unit.

Using the proposed method, it is possible to provide a trained function that may be used in the method for providing a prognosis data record.

In a further embodiment variant of the proposed computer-implemented method for providing the trained function, a training elastography data record relating to the examination region of the examination object may be received. In addition to this, the training elastography data record may be registered with the first training image data record. In addition, the input data may also be based on the training elastography data record. The training elastography data record may have, for example, all the properties of the elastography data record as described above in relation to the method for providing a prognosis data record and vice versa. For example, the training elastography data record may be an elastography data record.

In this case, the training elastography data record may include information about an elasticity and/or viscosity of at least one tissue region of the examination region. For example, the training elastography data record may include an assignment of an elastography value and/or elastography information to at least one tissue region; this is contained in the examination region, for example. The training elastography data record may include, for example, two-dimensional and/or three-dimensional medical image data relating to the examination region of the examination object. The training elastography data record may map the examination region of the examination object (e.g., preoperatively).

In this case, the training elastography data record relating to the examination region of the examination object may be recorded and/or provided (e.g., by a medical imaging device, such as preoperatively). The medical imaging device for recording the training elastography data record may take the form of a magnetic resonance system (MRT) and/or ultrasound device, for example. In addition to this, the training elastography data record may be simulated.

The receipt of the training elastography data record may include, for example, capture and/or readout from a computer-readable data store and/or receipt from a data storage unit (e.g., a database). In addition to this, the training elastography data record may be provided by a processing unit of the medical imaging device for recording the training elastography data record.

The input data of the trained function may also be based on the training elastography data record. As a result of taking the training elastography data record into account when creating the training prognosis data record, it is possible to achieve greater accuracy of the training prognosis data record with respect to a change influenced by the medical object at the examination region.

In addition to this, the registration of the training elastography data record with the first training image data record may be based, for example, on a specified anatomical structure and/or a predetermined tissue region (e.g., an ablation zone and/or ablation lesion) and/or a marker structure. In this case, the registration of the training elastography data record with the first training image data record may include a rigid and/or non-rigid transformation of the training elastography data record. For example, the registration of the training elastography data record with the first image data record may be effected in an image-based manner (e.g., based on anatomical and/or geometrical features).

In a further embodiment variant of the proposed computer-implemented method for providing the trained function, at least one second training image data record relating to at least one section of the examination region of the examination object may be received. The at least one second training image data record may have, for example, all the properties of the second training image data record as described above in relation to the method for providing a prognosis data record and vice versa. For example, the at least one training image data record may be a second image data record.

The at least one second training image data record may include, for example, two-dimensional and/or three-dimensional medical image data relating to at least one section of the examination region of the examination object. The at least one second training image data record may map the at least one section of the examination region of the examination object (e.g., intraoperatively and/or postoperatively). In addition, the at least one second training image data record may include, for example, a tissue parameter map and/or a temperature map. In this case, the at least one second training image data record may map a temporal change at the examination region of the examination object as a result of the medical object (e.g., as compared with the first training image data record). In addition to this, a predetermined and/or changed tissue region (e.g., an ablation zone and/or an ablation lesion) may be segmented and/or contrasted in the at least one second training image data record. Further, the at least one second training image data record may map the at least one section of the examination region of the examination object ex-vivo. For this, a tissue sample that originates from the examination region of the examination object, for example, may be mapped ex-vivo in the at least one second training image data record.

In this case, the at least one second training image data record relating to the examination region of the examination object may be recorded and/or provided, for example, by a medical imaging device. The medical imaging device for recording the at least one second training image data record may take the form of, for example, a medical x-ray device (e.g., a C-arm x-ray device and/or DynaCT) and/or a magnetic resonance system (MRT) and/or a computed tomography system (CT) and/or an ultrasound device.

The receipt of the at least one second training image data record may include, for example, capture and/or readout from a computer-readable data store and/or receipt from a data storage unit (e.g., a database). In addition to this, the at least one second training image data record may be provided by a processing unit of the medical imaging device for recording the at least one second training image data record.

In addition to this, the at least one second training image data record may be registered with the first training image data record. In this case, the registration of the at least one second training image data record with the first training image data record may be based, for example, on a specified anatomical structure and/or a predetermined tissue region (e.g., an ablation zone and/or ablation lesion) and/or a marker structure. In this case, the registration of the at least one second training image data record with the first training image data record may include a rigid and/or non-rigid transformation of the at least one second training image data record.

The input data of the trained function may also be based on the at least one second training image data record. As a result of taking the at least one second training image data record into account when creating the training prognosis data record, it is possible to achieve greater accuracy of the training prognosis data record with respect to a temporal change influenced by the medical object at the examination region.

In a further embodiment variant of the proposed computer-implemented method for providing a trained function, the at least one second training image data record may be recorded by an ultrasound device.

In this case, the at least one second training image data record may include, for example, two-dimensional and/or three-dimensional medical ultrasound image data relating to at least one section of the examination region of the examination object. In addition to this, a predetermined change of a tissue region that may be influenced by the medical object (e.g., an ablation zone and/or an ablation lesion and/or at least one fluid bubble) may be segmented and/or contrasted in the at least one second training image data record.

By this, a lesion formation and/or a fluid bubble formation (e.g., as a temporal change at the examination region of the examination object) may be mapped in the at least one second training image data record.

In this case, training positioning information of the ultrasound device at the instant of the recording of the at least one second training image data record may be captured by a position capturing unit (e.g., an electromagnetic and/or optical sensor). By this, it is possible to achieve a particularly accurate registration of the at least one second training image data record with the first training image data record.

In a further embodiment variant of the proposed computer-implemented method for providing a trained function, the training prognosis data record may include probability information and/or characteristic form information (e.g., about the temporal profile) of a fluid bubble formation and/or lesion formation within the examination region of the examination object.

In this case, the probability information may include, for example, a temporal and/or spatial progression model of the fluid bubble formation and/or lesion formation within the examination region of the examination object. For example, the training prognosis data record may include an assignment of in each case at least one probability value of a fluid bubble formation and/or lesion formation to at least one tissue region within the examination region. In addition to this, the training prognosis data record may include characteristic form information (e.g., a volume model) about a characteristic form of the fluid bubble formation and/or lesion formation within the examination region.

In this case, a fluid bubble may include, for example, a spatially enclosed gas and/or gas mixture and/or a liquid and/or a liquid mixture. In addition to this, a lesion and/or fluid bubble may be captured and/or presented, for example, by changed contrasting in at least one tissue region of the examination region as compared with the first training image data record.

In this case, all input data of the trained function, for example, may be taken into account for the purpose of improving an accuracy of the training prognosis data record. In this case, interpolation of the probability information and/or characteristic form information (e.g., in tissue regions of the examination region in which little or no fluid bubble formation and/or lesion formation is possible) may also be advantageous. For this, the training prognosis data record may be interpolated by applying, for example, an interpolation function.

In a further embodiment variant of the proposed computer-implemented method for providing a trained function, the training prognosis data record may have a validity range with respect to the at least one training operating parameter.

In this case, using the at least one training operating parameter as input data of the trained function, for example, a validity range (e.g., a definition range of the trained function) may be specified for the training prognosis data records that may be created. For example, an electrical current-strength range and/or an electrical voltage range and/or a temperature range and/or a magnetic field-strength range and/or an electrical field-strength range and/or a frequency range of the at least one training operating parameter of the respective medical object may specify the validity range of the training prognosis data record.

In addition to this, the training prognosis data record may include information about the validity range with respect to the at least one training operating parameter. In this case, for example, irrespective of the validity range, a training prognosis data record may be created by applying the trained function to input data. With reference to the information about the validity range contained in the training prognosis data record, it is possible to infer the validity of the training prognosis data record with respect to the at least one training operating parameter.

In a further embodiment variant of the proposed computer-implemented method for providing a trained function, the first training image data record may be recorded by a magnetic resonance system and/or a medical x-ray device and/or a computed tomography system. By this, a two-dimensional and/or three-dimensional mapping of the examination region of the examination object may be achieved in the first training image data record (e.g., pre-operatively).

In a third aspect, the present embodiments relate to a provision unit for providing a prognosis data record. In this case, the provision unit includes a computing unit and an interface. In addition to this, the interface is configured to receive a first image data record relating to the examination region of the examination object. In addition to this, the interface is configured to receive at least one operating parameter of a medical object that is arranged at the examination region and positioning information of the medical object that is arranged at the examination region. In addition, the computing unit is configured to create the prognosis data record by applying a trained function to input data. In this case, the input data is based on the first image data record and on the at least one operating parameter and the positioning information of the medical object. Further, at least one parameter of the trained function is based on a comparison with a first comparison image data record. In this case, as compared with the first image data record, the first comparison image data record includes changes influenced by the medical object at the examination region. In addition to this, the interface is configured to provide the prognosis data record.

Such a provision unit may be configured, for example, to execute the methods described above for providing a prognosis data record, and aspects of the methods. The provision unit is configured to execute these methods and aspects thereof by virtue of the interface and the computing unit being configured to execute the corresponding method acts.

In a fourth aspect, the present embodiments relate to a medical device including the proposed provision unit. In this case, the medical device is configured to control the medical object based on the prognosis data record. In addition to this, the medical device may take the form of, for example, a medical imaging device (e.g., a magnetic resonance system and/or a computed tomography system and/or an ultrasound device and/or a medical x-ray device).

The medical device may include, for example, a presentation unit (e.g., a display and/or a monitor) that is configured to output information and/or graphical presentations of information from the medical device and/or the provision unit and/or further components. For example, the presentation unit may be configured to output a graphical presentation of the prognosis data record.

The advantages of the proposed medical device correspond essentially to the advantages of the proposed computer-implemented method for providing a prognosis data record. Features, advantages, or alternative embodiment variants cited in this context may also be applied equally to the other claimed subject matter and vice versa.

In a fifth aspect, the present embodiments relate to a training unit for providing a trained function. In this case, the training unit includes a training interface and a training computing unit. In addition to this, the training interface is configured to receive a training image data record relating to an examination region of an examination object. In addition, the training interface is configured to receive at least one training operating parameter of a medical object that is arranged at the examination region of the examination object and training positioning information of the medical object that is arranged at the examination region. Further, the training interface is configured to receive a further training image data record relating to the examination region of the examination object. In this case, the further training image data record is recorded after the first training image data record in time. In addition to this, a change at the examination region of the examination object as a result of the medical object takes place after the recording of the first training image data record and before recording the further training image data record. Further, the training computing unit is also configured to create a further comparison prognosis data record from the further training image data record. In this case, as compared with the first training image data record, the further comparison prognosis data record includes changes influenced by the medical object at the examination region. In addition to this, the training computing unit is configured to create a training prognosis data record by applying the trained function to input data. In this case, the input data is based on the first training image data record and on the at least one training operating parameter and the training positioning information of the medical object. In addition, the training computing unit is configured to adjust at least one parameter of the trained function based on a comparison of the further comparison prognosis data record and the training prognosis data record. In addition to this, the training interface is configured to provide the trained function.

Such a training unit may be configured, for example, to execute the methods described above for providing a trained function, and aspects of the methods. The training unit is configured to execute these methods and aspects thereof by virtue of the training interface and the training computing unit being configured to execute the corresponding method acts.

In a sixth aspect, the present embodiments relate to a computer program product including a computer program that may be loaded directly into a memory of a provision system, with program sections for executing all acts of the method for providing a prognosis data record, or aspects of the method, when the program sections are executed by the provision unit. Alternatively or additionally, the computer program may be loaded directly into a training memory of a training unit, with program sections for executing all acts of the method for providing a trained function, or an aspect of the method, when the program sections are executed by the training unit.

In a seventh aspect, the present embodiments relates to a computer-readable storage medium that stores program sections that may be read and executed by a provision unit in order to execute all acts of the method for providing a prognosis data record, or aspects of the method, when the program sections are executed by the provision unit. Alternatively or additionally, the computer-readable storage medium may store program sections that may be read and executed by a training unit in order to execute all acts of the method for providing a trained function, or an aspect of the method, when the program sections are executed by the training unit.

In an eighth aspect, the present embodiments relate to a computer program or computer-readable storage medium including a trained function provided by a method for providing a trained function or by an aspect of the method.

A largely software-based realization has the advantage that provision units and/or training units already in use may also be upgraded easily by a software update in order to work in the manner of the present embodiments. In addition to the computer program, such a computer program product may optionally include additional parts such as, for example, documentation and/or additional components, and hardware components such as, for example, hardware keys (e.g., dongles etc.) for using the software.

BRIEF DESCRIPTION OF THE DRAWINGS

Exemplary embodiments of the invention are illustrated in the drawings and described in greater detail below. Same reference signs denote same features in the different figures, in which:

FIG. 4 shows a schematic flow diagram of a computer-implemented method for providing a prognosis data record relating to an examination object;

FIG. 5 shows a schematic flow diagram of a computer-implemented method for providing a trained function;

DETAILED DESCRIPTION

Figure 1:
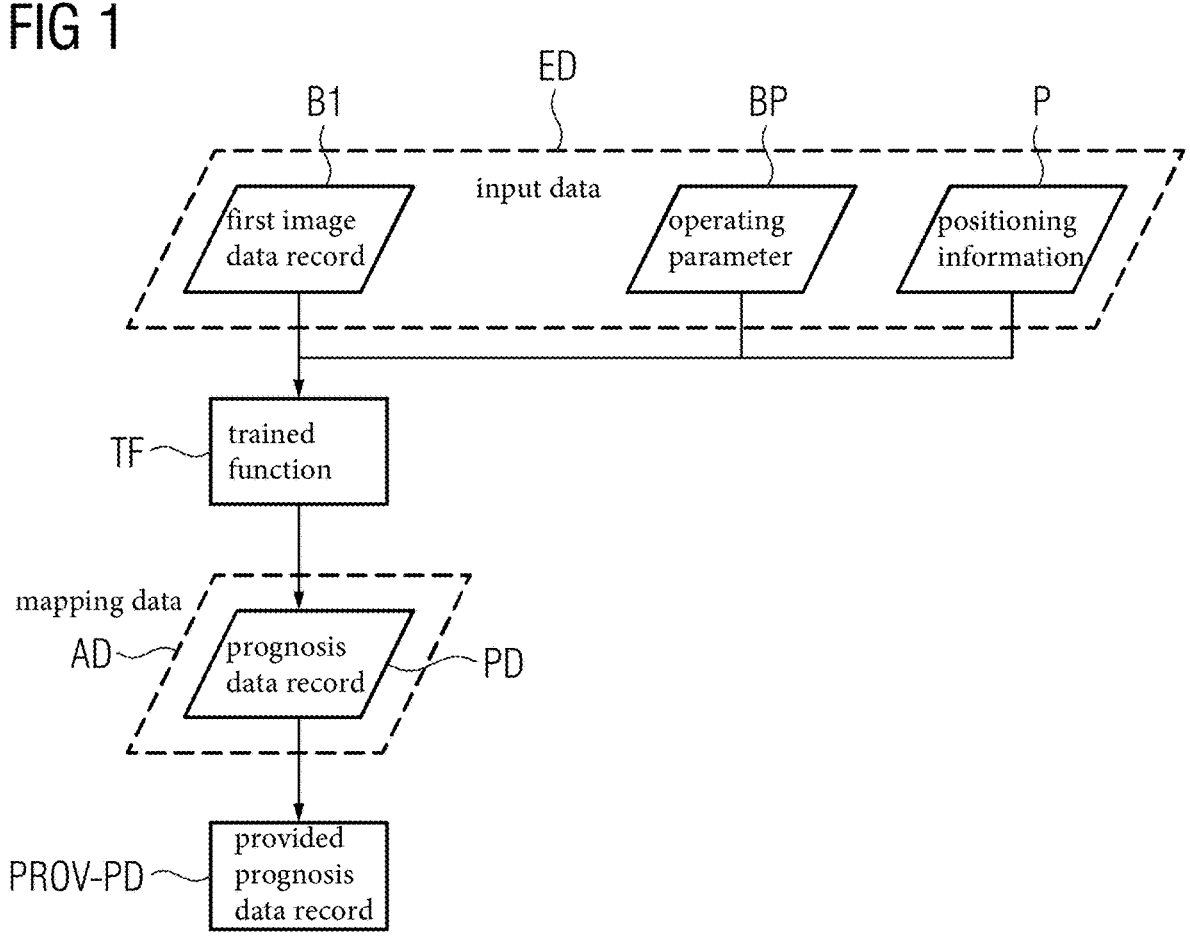
FIGS. 1 to 3 show schematic illustrations of a data flow in various embodiment variants of a computer-implemented method for providing a prognosis data record relating to an examination object.

FIG. 1 schematically depicts a data flow of a proposed computer-implemented method for providing a prognosis data record relating to an examination object. In this case, a first image data record B1 relating to an examination region of the examination object may be received. In addition to this, at least one operating parameter BP of a medical object that is arranged at the examination region of the examination object and positioning information P of the medical object that is arranged at the examination region of the examination object may be received. The prognosis data record PD may be created by applying a trained function TF to input data ED. In this context, the trained function TF may be a neural network (e.g., a convolutional neural network or a network including a convolutional layer).

In addition to this, the prognosis data record PD may be considered, for example, as mapping data AD of the trained function. In this case, the input data ED may be based on the first image data record B1 and on the at least one operating parameter BP and the positioning information P of the medical object. In addition to this, the at least one parameter of the trained function TF may be based on a comparison with a first comparison image data record. In this context, as compared with the first image data record B1, the first comparison image data record may include changes influenced by the medical object at the examination region. In addition, the prognosis data record PD may be provided PROV-PD.

In this case, the prognosis data record PD may include probability information and/or characteristic form information (e.g., about the temporal profile) of a fluid bubble formation and/or lesion formation within the examination region of the examination object. In addition, the prognosis data record PD may include a validity range with respect to the at least one operating parameter BP.

The first image data record B1 may be recorded by a magnetic resonance system and/or a medical x-ray device and/or a computed tomography system.

Figure 2:
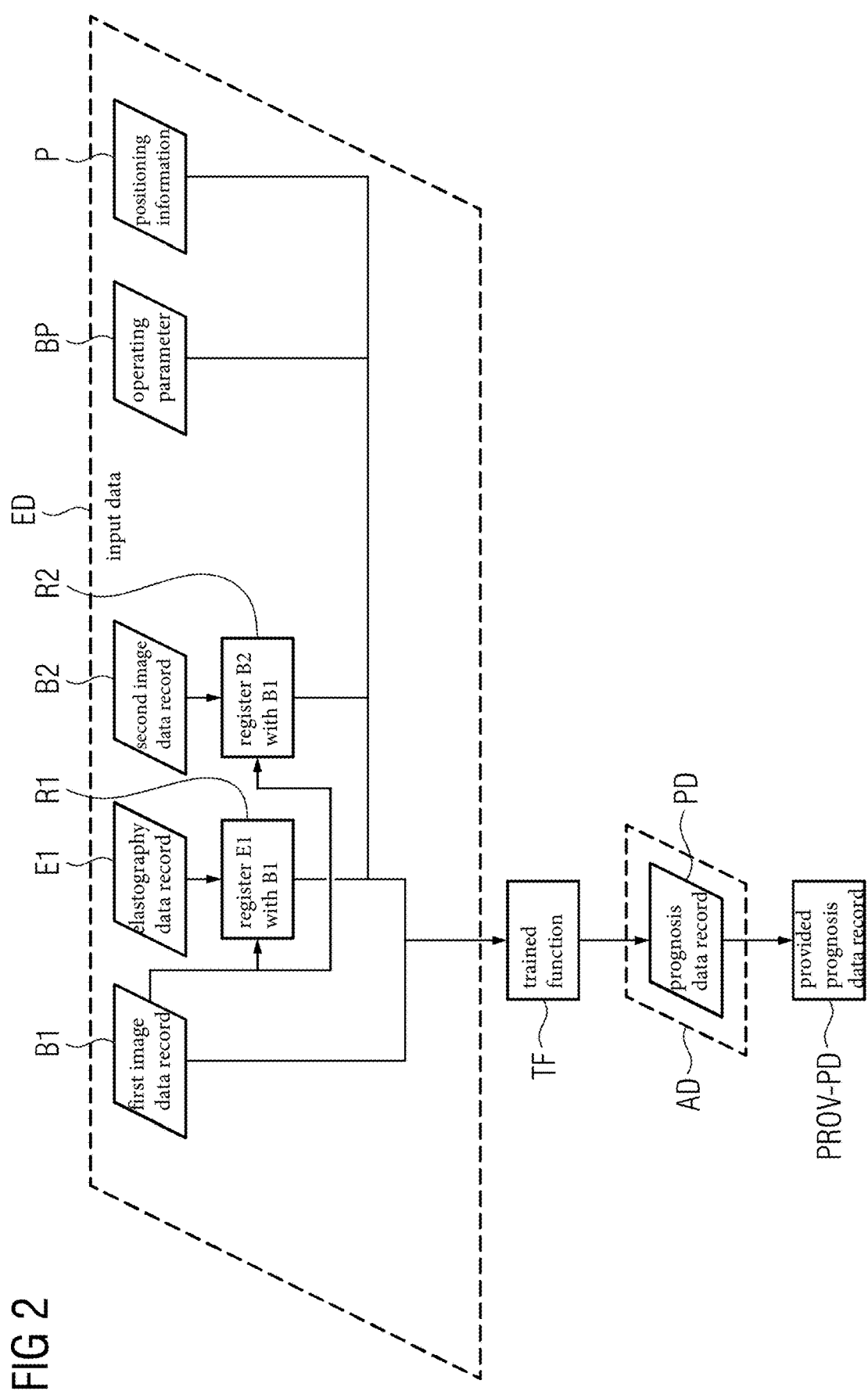

FIG. 2 schematically shows a data flow of a further embodiment variant of the proposed computer-implemented method for providing a prognosis data record PD relating to an examination object. In this case, an elastography data record E1 relating to the examination region of the examination object may also be received. In addition, the elastography data record E1 may be registered R1 with the first image data record B1. In addition to this, the input data ED of the trained function TF may also be based on the elastography data record E1.

Further, at least one second image data record B2 relating to at least one section of the examination region of the examination object may be received. In this case, the at least one second image data record B2 may map a temporal change at the examination region of the examination object as a result of the medical object. In addition to this, the at least one second image data record B2 may be registered R2 with the first image data record B1. In addition, the input data ED of the trained function TF may also be based on the at least one second image data record B2.

Figure 3:
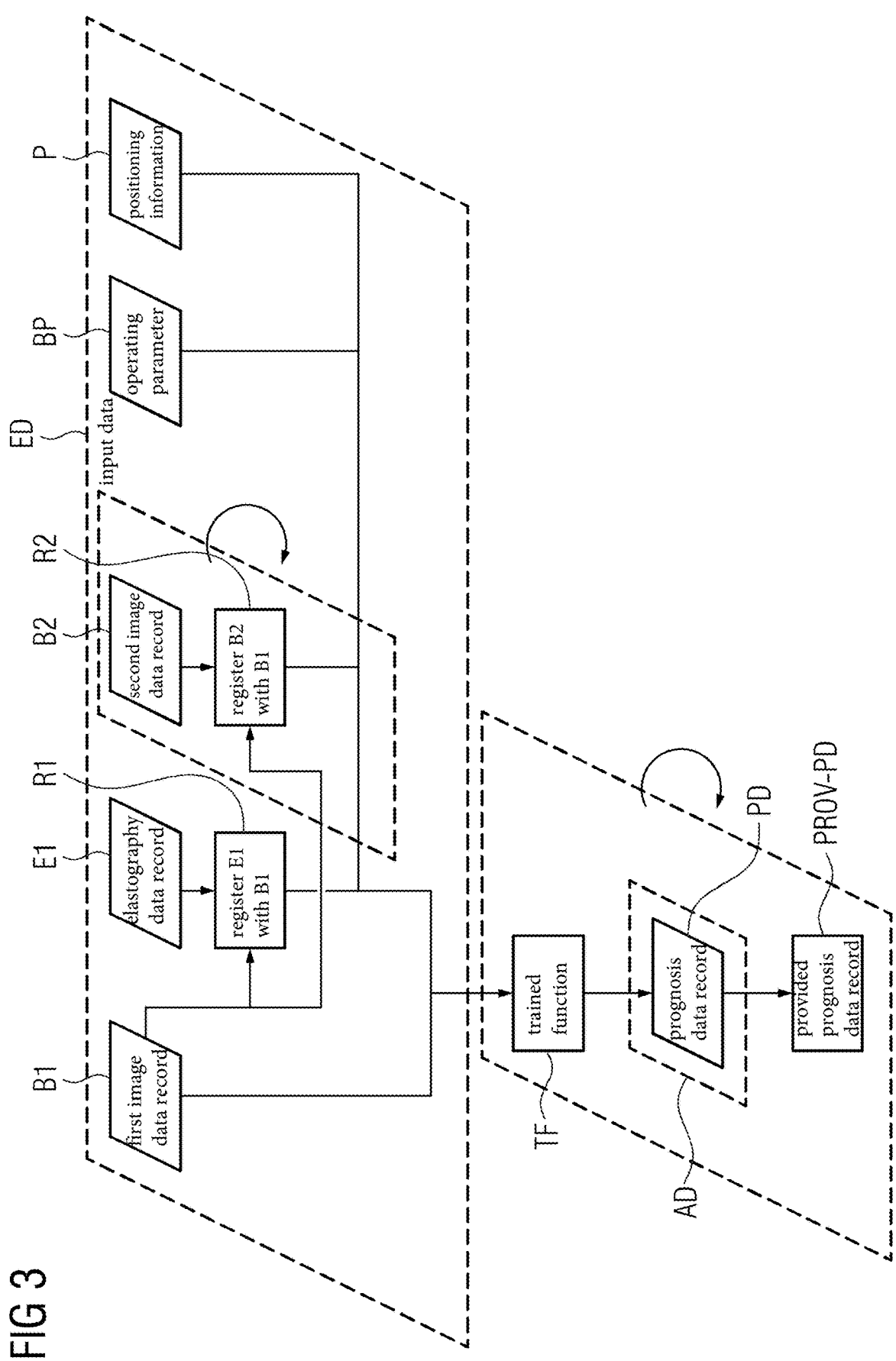

FIG. 3 schematically illustrates a data flow of a further embodiment variant of the proposed method for providing a prognosis data record PD. In this case, a plurality of second image data records B2 may be received in temporal sequence. In addition to this, a prognosis data record PD may be created in each case (e.g., iteratively) based on the second image data records B2 previously received in the temporal sequence.

FIG. 4 shows a schematic flow diagram of a computer-implemented method for providing a prognosis data record PD relating to an examination object. In this case, the first image data record B1, the at least one operating parameter BP, and positioning information P may be received in a first act REC-1.

The receipt may include, for example, capture and/or readout from a computer-readable data store and/or receipt from a data storage unit (e.g., a database). In addition to this, the first image data record B1 and/or the positioning information may be provided by a processing unit of the medical imaging device. In addition, the at least one operating parameter BP and/or the positioning information P may be provided by a processing unit (e.g., one or more processors) of the medical object.

In a further act DET-PD, the prognosis data record PD may be created by applying the trained function TF to the input data ED. After this, the prognosis data record PD may be provided PROV-PD.

FIG. 5 shows a schematic flow diagram of an embodiment variant of a computer-implemented method for providing a trained function TF. In this case, a first training image data record TB1 relating to an examination region of an examination object may be received.

The first training image data record TB1 may be recorded by a magnetic resonance system and/or a medical x-ray device and/or a computed tomography system.

In addition to this, at least one training operating parameter TBP and training positioning information TP of the medical object that is arranged at the examination region of the examination object may be received. In addition to this, a further training image data record WTB relating to the examination region of the medical object may be received. In this case, the further training image data record WTB may be recorded after the first training image data record TB1 in time (e.g., postoperatively). In addition to this, a change at the examination region of the examination object as a result of the medical object may take place after the recording of the first training image data record TB1 and before recording the further training image data record WTB. Further, a comparison prognosis data record VPD may be created F from the further training image data record WTB. In this case, as compared with the first training image data record TB1, the comparison prognosis data record VPD may include changes influenced by the medical object at the examination region. In addition to this, a training prognosis data record TPD may be created by applying the trained function TF to input data ED. In this case, the input data ED may be based on the first training image data record TB1 and on the at least one training operating parameter TBP and the training positioning information TP of the medical object. In this case, the training prognosis data record TPD may be considered as training mapping data TAD of the trained function TF.

In this case, the training prognosis data record TPD may include probability information and/or characteristic form information (e.g., about the temporal profile) of a fluid bubble formation and/or lesion formation within the examination region of the examination object. In addition, the training prognosis data record TPD may include a validity range with respect to the at least one training operating parameter TBP.

In addition, at least one parameter of the trained function TF may be adjusted ADJ-TF based on a comparison of the comparison prognosis data record VPD and the training prognosis data record TPD. After this, the trained function TF may be provided PROV-TF.

Further, the proposed computer-implemented method for providing a trained function TF may also include receipt of a training elastography data record (not shown here) relating to the examination region of the examination object. In addition to this, the training elastography data record may be registered with the first training image data record TB1. In addition, the input data ED of the trained function TF may also be based on the training elastography data record.

In addition to this, at least one second training image data record (not shown here) relating to at least one section of the examination region of the examination object may be received. In this case, the at least one second training image data record may map a temporal change at the examination region of the examination object as a result of the medical object. In addition to this, the input data ED of the trained function TF may also be based on the at least one second training image data record.

Figure 6:
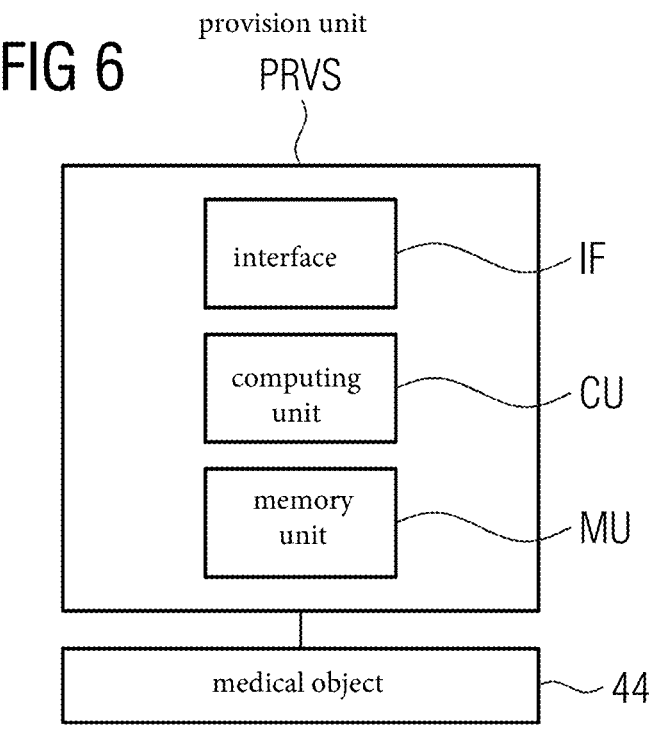
FIG. 6 shows an exemplary embodiment of a provision unit.
Figure 7:
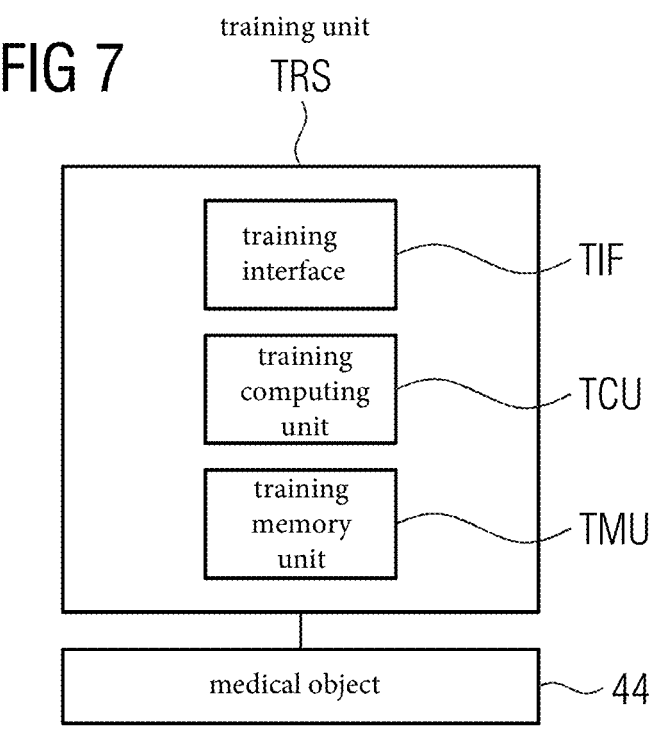
FIG. 7 shows an exemplary embodiment of a training unit.

FIG. 6 shows a provision unit PRVS, and FIG. 7 shows a training unit TRS. The illustrated provision unit PRVS may be configured to execute a computer-implemented method according to the present embodiments for providing a prognosis data record PD relating to an examination object. The illustrated training unit TRS may be configured to execute a proposed computer-implemented method for providing a trained function TF. The provision unit PRVS may include an interface IF, a computing unit CU, and a memory unit MU. In addition to this, the training unit TRS may include a training interface TIF, a training computing unit TCU, and a training memory unit TMU.

In this case, the interface IF may be configured to receive the first image data record B1 relating to the examination region of the examination object. In addition to this, the interface IF may be configured to receive the at least one operating parameter BP of the medical object that is arranged at the examination region of the examination object and the positioning information P of the medical object that is arranged at the examination region of the examination object. In addition, the computing unit CU may be configured to create DET-PD the prognosis data record PD by applying the trained function TF to the input data ED. In addition to this, the interface may be configured to provide PROV-PD the prognosis data record PD.

Further, the training interface TIF may be configured to receive the first training image data record TB1 relating to the examination region of the examination object. In addition, the training interface may be configured to receive the at least one training operating parameter TBP of the medical object that is arranged at the examination region of the examination object and the training positioning information TP of the medical object that is arranged at the examination region of the examination object. Further, the training interface TIF may be configured to receive the further training image data record WTB. In addition to this, the training computing unit may be configured to create F the comparison prognosis data record VPD from the further training image data record WTB. The training computing unit may also be configured to create the training prognosis data record TPD by applying the trained function TF to the input data ED. In addition to this, the training computing unit may be configured to adjust ADJ-TF the at least one parameter of the trained function TF. The training interface TIF may also be configured to provide PROV-TF the trained function TF.

The provision unit PRVS and/or the training unit TRS may be, for example, a computer, a microcontroller, or an integrated circuit. Alternatively, the provision unit PRVS and/or the training unit TRS may be a real or virtual framework of computers (e.g., a technical term for a real framework is a "cluster" and a technical term for a virtual framework is a "cloud"). The provision unit PRVS and/or the training unit TRS may also be configured as a virtual system that is executed on a real computer or on a real or virtual framework of computers (e.g., virtualization).

An interface IF and/or a training interface TIF may be a hardware or a software interface (e.g., PCI bus, USB or Firewire). A computing unit CU and/or a training computing unit TCU may include hardware elements or software elements (e.g., a microprocessor or a field programmable gate array (FPGA)). A memory unit MU and/or a training memory unit TMU may be realized as non-permanent working memory (e.g., random access memory (RAM)) or as permanent mass storage device (e.g., hard disk, USB stick, SD card, solid state disk).

The interface IF and/or the training interface TIF may include, for example, a plurality of sub-interfaces that execute different acts of the respective methods. In other words, the interface IF and/or the training interface TIF may also be provided as a number of interfaces IF or a number of training interfaces TIF. The computing unit CU and/or the training computing unit TCU may, for example, include a plurality of computing sub-units that execute the different acts of the respective methods. In other words, the computing unit CU and/or the training computing unit TCU may also be provided as a number of computing units CU or a number of training computing units TCU.

Figure 8:
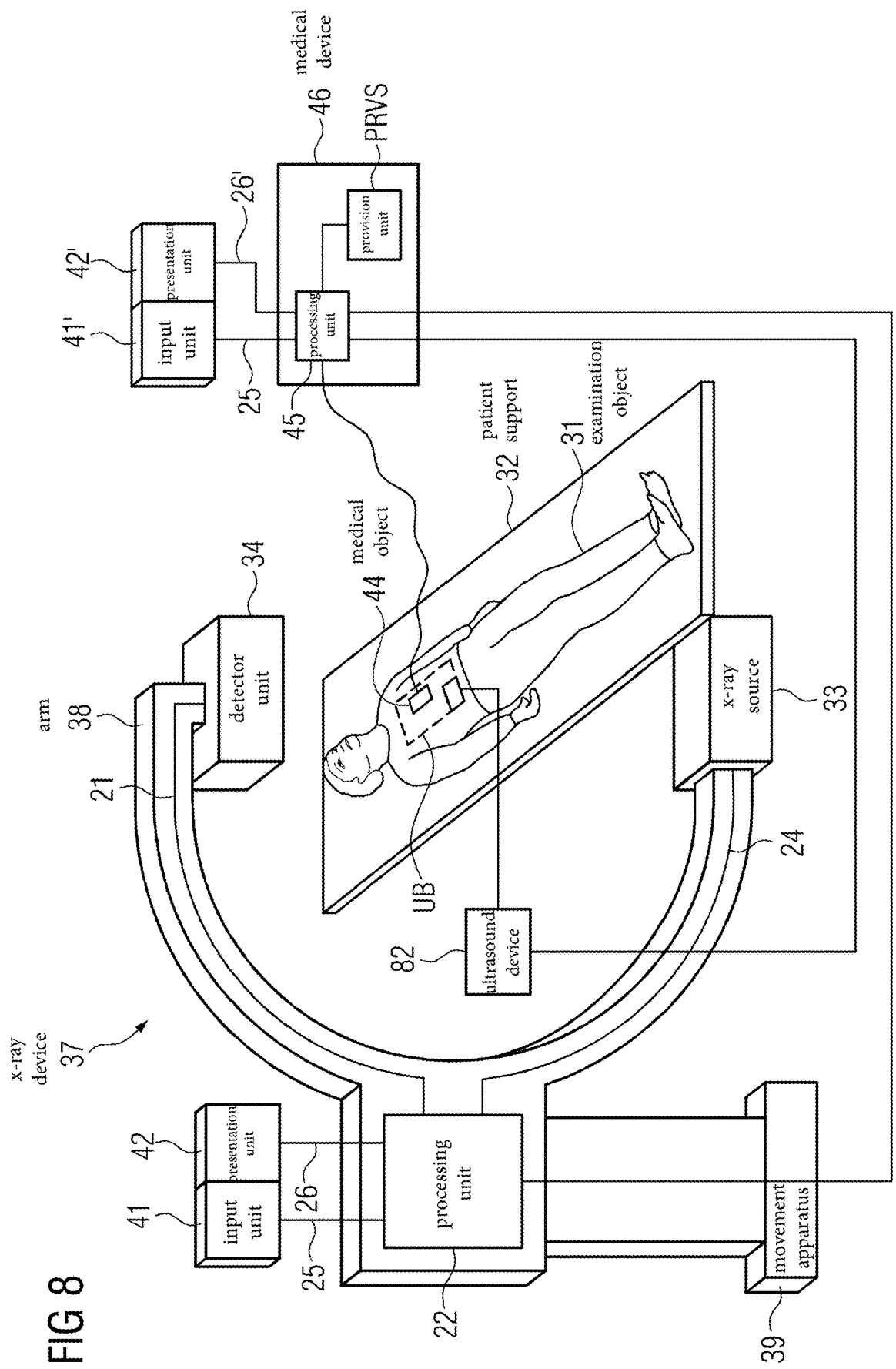
FIG. 8 shows a medical device for controlling a medical object based on the prognosis data record.

FIG. 8 schematically shows a medical device 46 for controlling the medical object 44 based on the prognosis data record PD. In this case, the medical device 46 may include a processing unit 45 and/or a proposed provision unit PRVS. The medical device may include a proposed training unit TRS (not shown here). The medical object 44 may include, for example, an ablation needle and/or a laparoscope and/or an endoscope and/or an electro-cauterizer and/or a catheter.

In addition to this, the first image data record B1 may be recorded by a medical x-ray device 37 (e.g., preoperatively). For example, a medical C-arm x-ray device 37 is schematically illustrated in FIG. 8 for this purpose. In this context, the medical C-arm x-ray device 37 includes a detector unit 34, an x-ray source 33, and a processing unit 22. For the purpose of recording the first image data record B1 (e.g., projection x-ray images and/or DynaCT images), the arm 38 of the C-arm x-ray device 37 may be so mounted as to allow movement about one or more axes. By this, it is possible to record the first image data record B1 (e.g., including a plurality of projection x-ray images each having different recording parameters, such as acquisition geometries). In addition to this, the medical C-arm x-ray device 37 may include a movement apparatus 39 that allows positional movement of the C-arm x-ray device 37.

For the purpose of recording the first image data record B1 relating to the examination region UB of the examination object 31, this being arranged on a patient support facility 32, the processing unit 22 may send a signal 24 to the x-ray source 33. The x-ray source 33 may then emit a beam of x-rays (e.g., a conical beam and/or fan beam). When the beam of x-rays, having interacted with the examination region UB of the examination object 31, strikes a surface of the detector unit 34, the detector unit 34 may send a signal 21 to the processing unit 22. For example, the processing unit 22 may receive the first image data record B1 based on the signal 21. Following thereupon, the processing unit 22 may provide the first image data record B1 to the processing unit 45 of the medical device 46.

Further, the medical C-arm x-ray device 37 may include an input unit 41 (e.g., a keypad) and/or a presentation unit 42 (e.g., a monitor and/or display). The input unit 41 may be integrated into the presentation unit 42 (e.g., in the case of a capacitive input display). In this case, control of the proposed method and/or the medical C-arm x-ray device 37 may be achieved by an input from an operator at the input unit 41. For example, a graphical presentation of the first image data record B1 may be output on the presentation unit 42.

In addition to this, the medical device 46 may include an input unit 41' (e.g., a keypad) and/or a presentation unit 42' (e.g., a monitor and/or display). The input unit 41' may be integrated into the presentation unit 42' (e.g., in the case of a capacitive input display). In this case, control of the proposed method and/or of the medical device 46 may be achieved by an input from an operator at the input unit 41'. For example, a graphical presentation of the prognosis data record PD may be output on the presentation unit 42'.

The processing unit 45 may provide the received first image data record B1 to the provision unit PRVS. The provision unit PRVS may then execute an embodiment variant of the proposed computer-implemented method for providing a prognosis data record PD relating to the examination object 31. In this case, the provision unit PRVS may additionally provide PROV-PD the prognosis data record PD that has been created to the processing unit 45 of the medical device 46. Based on the prognosis data record PD, the processing unit 45 may allow closed-loop or open-loop control of the medical object 44.

Further, the at least one second image data record B2 may be recorded by an ultrasound device 82. For this, the ultrasound device 82 may be arranged at the examination region UB of the examination object 31. In addition to this, the ultrasound device 82 may provide the at least one second image data record B2, which is recorded intraoperatively, for example, to the processing unit 45 of the medical device 46. In addition to this, the processing unit 45 may provide the at least one second image data record B2 to the provision unit PRVS.

In a similar manner to the recording and provision of the at least one second image data record B2, the at least one second training image data record may be recorded by the ultrasound device 82 and provided to the training unit TRS.

Further, the ultrasound device 82 may be configured to record the elastography data record E1. In this case, the recorded elastography data record E1 may be provided to the provision unit PRVS in a similar manner to the at least one second image data record B2. In a similar manner to the recording and provision of the elastography data record E1, the training elastography data record may be recorded by the ultrasound device 82 and provided to the training unit TRS.

The schematic illustrations contained in the figures described above do not in any way indicate scale or measurement ratios.

The methods described in detail above and the illustrated apparatuses are merely exemplary embodiments that may be modified in all manner of ways by a person skilled in the art without departing from the scope of the invention. The use of the indefinite article "a" or "an" does not preclude multiple instances of the features concerned. Equally, the terms "unit" and "element" do not preclude the respective components consisting of a plurality of interacting sub-components, which may also be physically distributed if applicable.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A computer-implemented method for providing a prognosis data record relating to an examination object, the computer-implemented method comprising:
   receiving a first image data record relating to an examination region of the examination object;
   receiving at least one operating parameter of a medical object that is arranged at the examination region of the examination object and positioning information of the medical object that is arranged at the examination region of the examination object;
   creating the prognosis data record, creating the prognosis data record comprising applying a trained function to input data, wherein the input data is based on the first image data record, the at least one operating parameter, and the positioning information of the medical object, wherein at least one parameter of the trained function is based on a comparison with a first comparison image data record, and wherein as compared with the first image data record, the first comparison image data record includes changes influenced by the medical object at the examination region; and
   providing the prognosis data record,
   wherein the prognosis data record includes:
      probability information of a fluid bubble formation within the examination region of the examination object, characteristic form information of the fluid bubble formation, or the probability information and the characteristic form information of the fluid bubble formation;
      probability information of a lesion formation within the examination region of the examination object, characteristic form information of the lesion formation, or the probability information and the characteristic form information of the lesion formation; or
      a combination thereof.

2. The computer-implemented method of claim 1, further comprising:
   receiving an elastography data record relating to the examination region of the examination object; and
   registering the elastography data record with the first image data record,
   wherein the input data is also based on the elastography data record.

3. The computer-implemented method of claim 1, further comprising:
   receiving at least one second image data record relating to at least one section of the examination region of the examination object,
   wherein the at least one second image data record maps a temporal change at the examination region of the examination object as a result of the medical object, and
   wherein the input data is also based on the at least one second image data record.

4. The computer-implemented method of claim 1, wherein the prognosis data record includes a validity range with respect to the at least one operating parameter.

5. The computer-implemented method of claim 1, wherein the first image data record is recorded by a magnetic resonance system, a medical x-ray device, a computed tomography system, or any combination thereof.

6. The computer-implemented method of claim 1, wherein receiving the first image data record comprises receiving, by an interface of a provision unit, the first image data record relating to the examination region of the examination object,
   wherein receiving the at least one operating parameter of the medical object that is arranged at the examination region of the examination object and the positioning information of the medical object that is arranged at the examination region of the examination object comprises receiving, by the interface, the at least one operating parameter of the medical object that is arranged at the examination region of the examination object and the positioning information of the medical object that is arranged at the examination region of the examination object,
   wherein creating the prognosis data record comprises creating, by a computing unit of the provision unit, the prognosis data record, and
   wherein providing the prognosis data record comprises providing, by the interface, the prognosis data record.

7. The computer-implemented method of claim 3, wherein the at least one second image data record is recorded by an ultrasound device.

8. The computer-implemented method of claim 3, wherein receiving the at least one second image data record comprises receiving a plurality of second image data records in temporal sequence, and
   wherein a prognosis data record is created in each case based on the second image data records previously received in the temporal sequence.

9. The computer-implemented method of claim 6, wherein the provision unit is part of a medical device.

10. A computer-implemented method for providing a trained function, the computer-implemented method comprising:
   receiving a first training image data record relating to an examination region of an examination object;
   receiving at least one training operating parameter of a medical object that is arranged at the examination region of the examination object and training positioning information of the medical object that is arranged at the examination region of the examination object;
   receiving a further training image data record relating to the examination region of the examination object, wherein the further training image data record is recorded after the first training image data record in time, wherein a change at the examination region of the examination object as a result of the medical object takes place after the recording of the first training image data record and before recording the further training image data record;
   creating a comparison prognosis data record from the further training image data record, wherein as compared with the first training image data record, the comparison prognosis data record includes changes influenced by the medical object at the examination region;
   creating a training prognosis data record, creating the training prognosis data record comprising applying the trained function to input data, wherein the input data is based on the first training image data record, the at least one training operating parameter, and the training positioning information of the medical object;

adjusting at least one parameter of the trained function based on a comparison of the comparison prognosis data record and the training prognosis data record; and providing the trained function, wherein the training prognosis data record includes:
probability information of a fluid bubble formation within the examination region of the examination object, characteristic form information of the fluid bubble formation, or the probability information and the characteristic form information of the fluid bubble formation;

probability information of a lesion formation within the examination region of the examination object, characteristic form information of the lesion formation, or the probability information and the characteristic form information of the lesion formation; or a combination thereof.

11. The computer-implemented method of claim 10, further comprising:
receiving a training elastography data record relating to the examination region of the examination object;
and registering the training elastography data record with the first training image data record,
wherein the input data is also based on the training elastography data record.

12. The computer-implemented method of claim 10, further comprising receiving at least one second training image data record relating to at least one section of the examination region of the examination object,
wherein the at least one second training image data record maps a temporal change at the examination region of the examination object as a result of the medical object, and
wherein the input data is also based on the at least one second training image data record.

13. The computer-implemented method of claim 10, wherein the training prognosis data record includes a validity range with respect to the at least one training operating parameter.

14. The computer-implemented method of claim 10, wherein the first training image data record is recorded by a magnetic resonance system, a medical x-ray device, a computed tomography system, or any combination thereof.

15. The computer-implemented method of claim 10, wherein receiving the first training image data record comprises receiving, by a training interface of a training unit, the first training image data record relating to the examination region of the examination object,
wherein receiving the at least one training operating parameter of the medical object that is arranged at the examination region of the examination object and the training positioning information of the medical object that is arranged at the examination region of the examination object comprises receiving, by the training interface, the at least one training operating parameter of the medical object that is arranged at the examination region of the examination object and the training positioning information of the medical object that is arranged at the examination region of the examination object, wherein receiving the further training image data record relating to the examination region of the examination object comprises receiving, by the training interface, the further training image data record relating to the examination region of the examination object, wherein creating the comparison prognosis data record from the further training image data record comprises creating, by a training computing unit of the training unit, the comparison prognosis data record from the further training image data record, wherein creating the training prognosis data record comprises creating, by the training computing unit, the training prognosis data record, wherein adjusting the at least one parameter of the trained function comprises adjusting, by the training computing unit, the at least one parameter of the trained function, and wherein providing the trained function comprises providing, by the training interface, the trained function.

16. The computer-implemented method of claim 12, wherein the at least one second training image data record is recorded by an ultrasound device.

17. In a non-transitory computer-readable storage medium that stores instructions executable by a provision unit to provide a prognosis data record relating to an examination object, the instructions comprising:
receiving a first image data record relating to an examination region of the examination object;
receiving at least one operating parameter of a medical object that is arranged at the examination region of the examination object and positioning information of the medical object that is arranged at the examination region of the examination object;
creating the prognosis data record, creating the prognosis data record comprising applying a trained function to input data, wherein the input data is based on the first image data record, the at least one operating parameter, and the positioning information of the medical object, wherein at least one parameter of the trained function is based on a comparison with a first comparison image data record, and wherein as compared with the first image data record, the first comparison image data record includes changes influenced by the medical object at the examination region; and
providing the prognosis data record,
wherein the prognosis data record includes:
probability information of a fluid bubble formation within the examination region of the examination object, characteristic form information of the fluid bubble formation, or the probability information and the characteristic form information of the fluid bubble formation;
probability information of a lesion formation within the examination region of the examination object, characteristic form information of the lesion formation, or the probability information and the characteristic form information of the lesion formation; or
a combination thereof.

* * * * *